United States Patent
Hatada et al.

(10) Patent No.: US 6,803,222 B2
(45) Date of Patent: Oct. 12, 2004

(54) ALKALINE PROTEASES

(75) Inventors: Yuji Hatada, Mihara (JP); Akinori Ogawa, Tochigi (JP); Yasushi Kageyama, Tochigi (JP); Tsuyoshi Sato, Tochigi (JP); Hiroyuki Araki, Tochigi (JP); Nobuyuki Sumitomo, Tochigi (JP); Mitsuyoshi Okuda, Tochigi (JP); Katsuhisa Saeki, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/985,689

(22) Filed: Nov. 5, 2001

(65) Prior Publication Data

US 2003/0022351 A1 Jan. 30, 2003

(30) Foreign Application Priority Data

Nov. 22, 2000 (JP) ...................................... 2000-355166
Apr. 12, 2001 (JP) ...................................... 2001-114048

(51) Int. Cl.$^7$ .............................. C12N 9/48; C11D 3/00
(52) U.S. Cl. ........................ 435/212; 510/276; 510/300
(58) Field of Search .......................................... 435/212

(56) References Cited

FOREIGN PATENT DOCUMENTS

| | | |
|---|---|---|
| EP | 0 130 756 | 1/1985 |
| EP | 0 204 342 | 12/1986 |
| EP | 0 251 446 | 1/1988 |
| EP | 1 029 920 | 8/2000 |
| JP | 4-197182 | 7/1992 |
| JP | 5-211868 | 8/1993 |
| JP | 6-70765 | 3/1994 |
| JP | 9-121855 | 5/1997 |
| JP | 9-121856 | 5/1997 |
| WO | WO 88/01293 | 2/1988 |
| WO | WO 91/00345 | 1/1991 |
| WO | WO 92/08778 | 5/1992 |
| WO | WO 92/21760 | 12/1992 |
| WO | WO 94/02618 | 2/1994 |
| WO | WO 95/30010 | 11/1995 |
| WO | WO 96/28556 | 9/1996 |
| WO | WO 98/56927 | 12/1998 |
| WO | WO 99/18218 | 4/1999 |
| WO | WO 99/20723 | 4/1999 |
| WO | WO 99/49056 | 9/1999 |
| WO | WO 99/49057 | 9/1999 |

OTHER PUBLICATIONS

Tobe et al, 1997 EMBL Acc# .E03808 Alignment with SID NO: 1.*
Christianson et al, 1998 from WO9856927. Alignment with NO: 1.*
Hitomi et al, 1999 from WO9918218. Alignment with SEQ ID NO: 1.*
R. J. Siezen, et al., Protein Engineering, vol. 4, No. 7, pp. 719–737, XP–0022008733, "Homology Modelling and Protein Engineering Strategy of Subtilases, The Family of Subtilisin–like Serine Proteinases", 1991.
R. J. Siezn, et al., Protein Science, vol. 6, No. 3, pp. 501–523, XP–000990399, "Subtilases: The Superfamily of Subtilisin–like Serine Proteases", Mar. 1997.
D. A. Estell, et al., The Journal of Biological Chemistry, vol. 260, No. 11, pp. 6518–6521, XP–000576091, "Engineering an Enzyme by Site–Directed Mutagenesis to be Resistant to Chemical Oxidation", Jun. 10, 1985.
K. Saeki, et al., Biochemical and Biophysical Research Communications, vol. 279, No. 2, pp. 313–319, XP–002238277, "Novel Oxidatively Stable Subtilisin–like Serine Proteases from Alkaliphilic *Bacillus* SPP: Enzymatic Properties, Sequences, and Evolutionary Relationships", Dec. 20, 2000.

* cited by examiner

*Primary Examiner*—Rebecca E. Prouty
*Assistant Examiner*—Sheridan Swope
(74) *Attorney, Agent, or Firm*—Oblon, Spivak, McClelland, Maier & Neustadt, P.C.

(57) ABSTRACT

The present invention relates to alkaline proteases having high specific activity and strong oxidant resistance. The present invention also relates to alkaline proteases having excellent detergency that is to be added to a detergent.

12 Claims, 4 Drawing Sheets

ALKALINE PROTEASES

TECHNICAL FIELD

The present invention relates to alkaline proteases having high specific activity and strong oxidant resistance. As the alkaline proteases of the present invention have an excellent detergency, these enzymes may be added to a detergent.

BACKGROUND ART

Proteases have conventionally been used in a variety of fields such as various detergents (including laundry detergents), cosmetics, bath agents, food modifiers, and pharmaceuticals (such as digestion aids and anti-inflammatory agents). Of these uses, proteases for detergents are industrially produced in the largest amount and have a great market value. Accordingly, a number of proteases are now available on the market.

In most cases, stains on clothes contain not only proteins but also plural components such as lipids and solid particles. Therefore, there is a demand for detergents having a sufficient detergency to remove complex stains. To address this demand, the present inventors applied for a patent (WO99/18218), which provided alkaline proteases having a molecular weight of about 43,000 that are capable of retaining caseinolytic activity even in the presence of a high concentration of fatty acids. The alkaline protease provided in WO99/18218 also exhibited excellent detergency even when the stain is composed of not a simple protein component but plural components, for example, protein and lipid.

Alkaline proteases having improved specific activity, oxidant resistance and detergency that are usable for detergents of wide-ranging compositions remain in demand.

DISCLOSURE OF THE INVENTION

The present inventors searched for improved alkaline proteases to address the aforementioned demand mainly from enzyme variants. The above-described alkaline proteases possess significant differences in enzymological properties from serine proteases typified by subtilisin. Accordingly, the modified site of subtilisin did not provide useful information. As a result of a further investigation, the present inventors have found that in order to obtain novel alkaline proteases having improved specific activity, stability against an oxidant and detergency while maintaining the properties of the above-described alkaline proteases, specific amino acid residues must be present at a predetermined position of their amino acid sequence.

In one aspect of the present invention, is an alkaline protease wherein an amino acid residue at (a) position 84, (b) position 104, (c) position 256 or (d) position 369 of SEQ ID NO:1, or at a position corresponding thereto, has been deleted or specifically mutated.

In the case of position 84 of SEQ ID NO:1, or a position corresponding thereto, the preferred mutation is to replace the original amino acid present in the sequence with an arginine, residue.

In the case of position 104 of SEQ ID NO:1, or a position corresponding thereto, the preferred mutation is to replace the original amino acid present in the sequence with a proline residue.

In the case of position 256 of SEQ ID NO:1, or a position corresponding thereto, the preferred mutation is to replace the original amino acid present in the sequence with an alanine, serine, glutamine, valine, leucine, asparagine, glutamic acid or aspartic acid residue.

In the case of position 369 of SEQ ID NO:1, or a position corresponding thereto, the preferred mutation is to replace the original amino acid present in the sequence with asparagine residue.

In another aspect of the present invention, is an alkaline protease wherein an amino acid residue at (e) position 66 or 264, (f) position 57, each of 101 to 106, 136, 193 or 342, (g) position 46 or 205, (h) position 54, 119, 138, 148 or 195, (i) position 247, (j) position 124, (k) position 107 or (l) position 257 of SEQ ID NO:1, or at a position corresponding thereto, has been deleted or specifically mutated.

In the case of Position 66 or 264 of SEQ ID NO:1, or a position corresponding thereto, the preferred mutation is to replace the original amino acid present in the sequence with a glutamine, aspartic acid, serine, glutamic acid, alanine, threonine, leucine, methionine, cysteine, valine, glycine or isoleucine residue.

In the case of position 57, 101 to 106, 136, 193, or 342 of SEQ ID NO:1, or a position corresponding thereto, the preferred mutation is to replace the original amino acid present in the sequence with a lysine, serine, glutamine, phenylalanine, valine, arginine, tyrosine, leucine, isoleucine, threonine, methionine, cysteine, tryptophan, aspartic acid, glutamic acid, histidine, proline or alanine residue.

In the case of position 46 or 205 of SEQ ID NO:1, or a position corresponding thereto, the preferred mutation is to replace the original amino acid present in the sequence with a tyrosine, tryptophan, alanine, asparagine, glutamic acid, threonine, valine, leucine, isoleucine, histidine, serine, lysine, glutamine, methionine or cysteine residue.

In the case of position 54, 119, 138, 148, or 195 of SEQ ID NO:1, or a position corresponding thereto, the preferred mutation is to replace the original amino acid present in the sequence with a tryptophan, phenylalanine, alanine, asparagine, glutamic acid, threonine, valine, histidine, serine, lysine, glutamine, methionine, glycine, aspartic acid, proline, arginine or cysteine residue.

In the case of position 247 of SEQ ID NO:1, or a position corresponding thereto, the preferred mutation is to replace the original amino acid present in the sequence with a tryptophan, phenylalanine, alanine, asparagine, glutamic acid, threonine, valine, leucine, isoleucine, histidine, serine, glutamine, methionine or cysteine residue.

In the case of position 124 of SEQ ID NO:1, or a position corresponding thereto, the preferred mutation is to replace the original amino acid present in the sequence with an alanine or lysine residue.

In the case of position 107 of SEQ ID NO:1, or a position corresponding thereto, the preferred mutation is to replace the original amino acid present in the sequence with a lysine, arginine, alanine or serine residue.

In the case of position 257 of SEQ ID NO:1, or a position corresponding thereto, the preferred mutation is to replace the original amino acid present in the sequence with a valine or isoleucine residue.

In a further aspect of the present invention, is a gene encoding the alkaline protease, a recombinant vector containing the gene and a transformant containing the vector.

In a still further aspect of the present invention, is a detergent composition containing the alkaline protease of the present invention.

BRIEF DESCRIPTION OF THE DRAWINGS

FIG. 1 is a diagram illustrating detergency of an alkaline protease. In each of FIG. 1A–1D detergency is illustrated for a deterrent lacking the addition of an alkaline protease and a detergent to which the wild type alkaline protease (KP43) is added.

BEST MODE FOR CARRYING OUT THE INVENTION

Figure 1A:
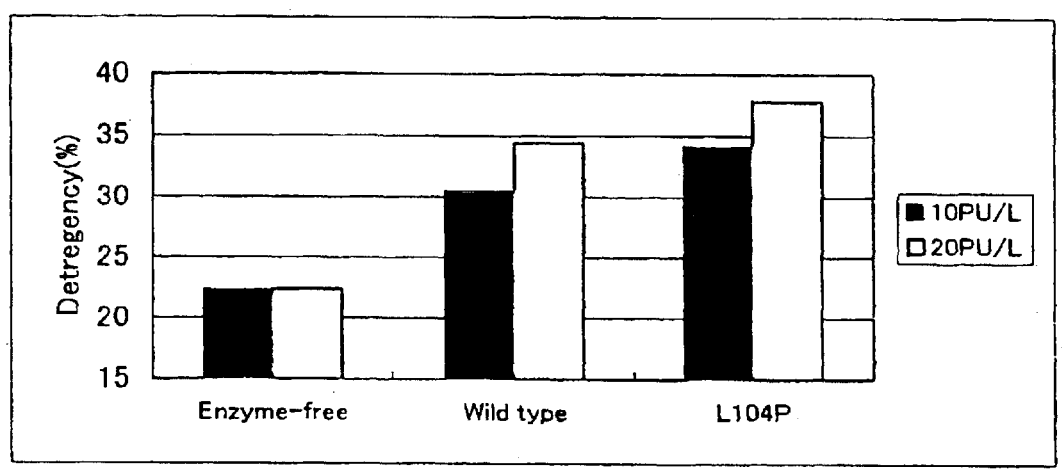
FIG. 1A illustrates the detergency for the L104P alkaline protease mutant.
Figure 1B:
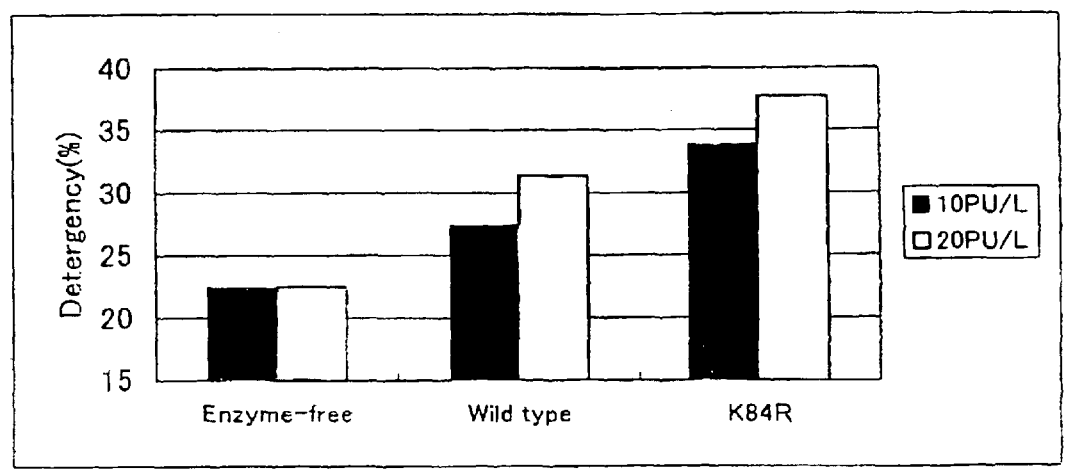
FIG. 1B illustrates the detergency for the K84R alkaline protease mutant.
Figure 1C:
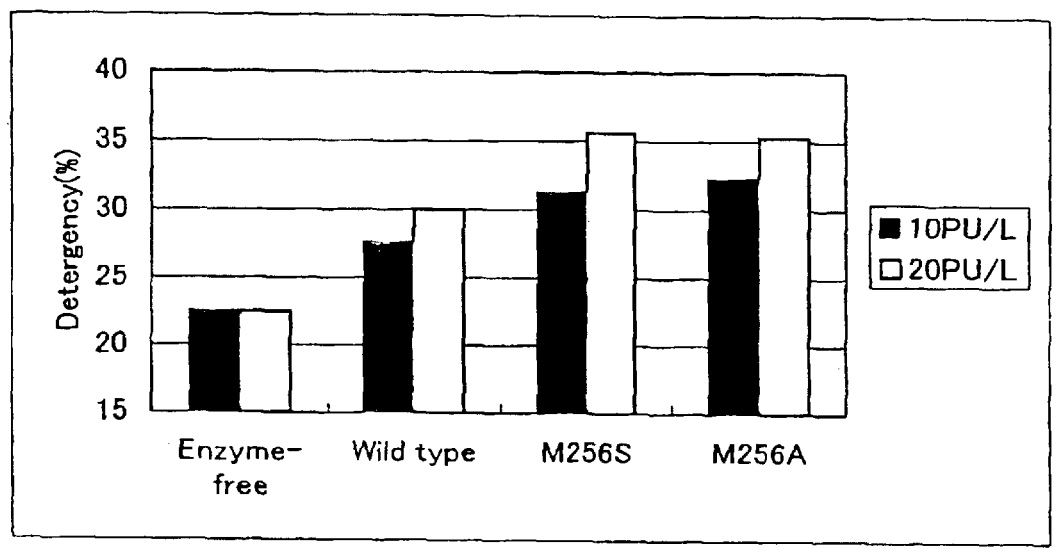
FIG. 1C illustrates the detergency for the M256S and M256A alkaline protease mutants.
Figure 1D:
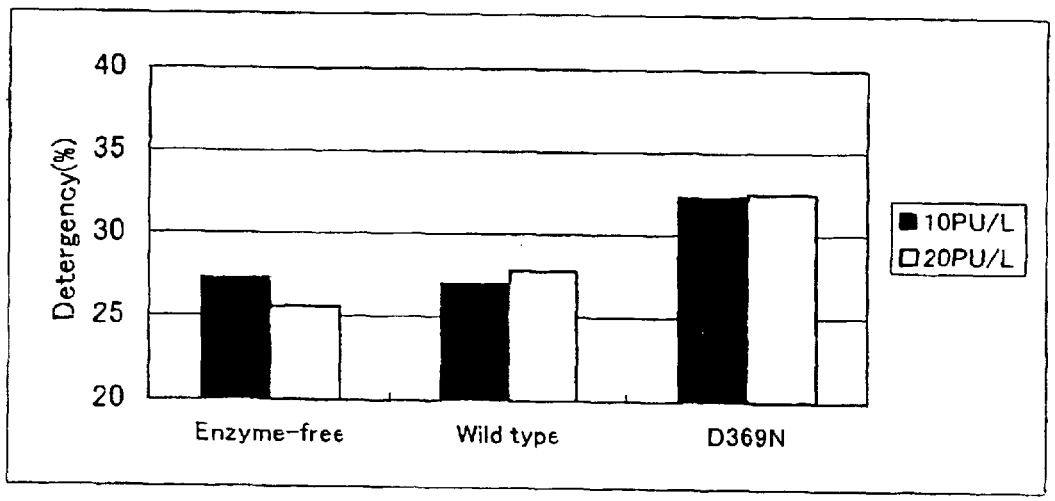
FIG. 1D illustrates the detergency for the D369N alkaline protease mutant.

As described above, the alkaline proteases of the present invention includes a deletion or specific mutation of an amino acid residue at (a) position 84, (b) position 104, (c) position 256 or (d) position 369 of SEQ ID NO:1 or at a position corresponding thereto.

In the case of position 84 of SEQ ID NO:1, or a position corresponding thereto, the preferred mutation is to replace the original amino acid present in the sequence with an arginine residue.

In the case of position 104 of SEQ ID NO:1, or a position corresponding thereto, the preferred mutation is to replace the original amino acid present in the sequence with a proline residue.

In the case of position 256 of SEQ ID NO:1, or a position corresponding thereto, the preferred mutation is to replace the original amino acid present in the sequence with an alanine, serine, glutamine, valine, leucine, asparagine, glutamic acid or aspartic acid residue.

In the case of position 369 of SEQ ID NO:1, or a position corresponding thereto, the preferred mutation is to replace the original amino acid present in the sequence with an asparagine residue.

In addition, as described above, the alkaline proteases of the present invention may includes a deletion or specific mutation of an amino acid residue at (e) position 66 or 264, (f) position 57, each of 101 to 106, 136, 193 or 342, (g) position 46 or 205, (h) position 54, 119, 138, 148 or 195, (i) position 247, (j) position 124, (k) position 107 or (l) position 257 of SEQ ID NO:1 or at a position corresponding thereto.

In the case of Position 66 or 264 of SEQ ID NO:1, or a position corresponding thereto, the preferred mutation is to replace the original amino acid present in the sequence with a glutamine, aspartic acid, serine, glutamic acid, alanine, threonine, leucine, methionine, cysteine, valine, glycine or isoleucine, residue.

In the case of position 57, 101 to 106, 136, 193, or 342 of SEQ ID NO:1, or a position corresponding thereto, the preferred mutation is to replace the original amino acid present in the sequence with a lysine, serine, glutamine, phenylalanine, valine, arginine, tyrosine, leucine, isoleucine, threonine, methionine, cysteine, tryptophan, aspartic acid, glutamic acid, histidine, proline or alanine residue.

In the case of position 46 or 205 of SEQ ID NO:1, or a position corresponding thereto, the preferred mutation is to replace the original amino acid present in the sequence with a tyrosine, tryptophan, alanine, asparagine, glutamic acid, threonine, valine, leucine, isoleucine, histidine, serine, lysine, glutamine, methionine or cysteine residue.

In the case of position 54, 119, 138, 148, or 195 of SEQ ID NO:1, or a position corresponding thereto, the preferred mutation is to replace the original amino acid present in the sequence with a tryptophan, phenylalanine, alanine, asparagine, glutamic acid, threonine, valine, histidine, serine, lysine, glutamine, methionine, glycine, aspartic acid, proline, arginine or cysteine residue.

In the case of position 247 of SEQ ID NO:1, or a position corresponding thereto, the preferred mutation is to replace the original amino acid present in the sequence with a tryptophan, phenylalanine, alanine, asparagine, glutamic acid, threonine, valine, leucine, isoleucine, histidine, serine, glutamine, methionine or cysteine residue.

In the case of position 124 of SEQ ID NO:1, or a position corresponding thereto, the preferred mutation is to replace the original amino acid present in the sequence with an alanine or lysine residue.

In the case of position 107 of SEQ ID NO:1, or a position corresponding thereto, the preferred mutation is to replace the original amino acid present in the sequence with a lysine, arginine, alanine or serine residue.

In the case of position 257 of SEQ ID NO:1, or a position corresponding thereto, the preferred mutation is to replace the original amino acid present in the sequence with a valine or isoleucine residue.

Specifically, the alkaline proteases according to the present invention include alkaline proteases having an amino acid sequence represented by SEQ ID NO:1wherein the amino acid residue at a position selected from the above-described (a) to (d) and (e) to (l) has been deleted or predetermined. In addition, the alkaline proteases according to the present invention include another alkaline protease wherein the amino acid residue at a position corresponding to a position selected from the above-described (a) to (d) and (e) to (l) has been deleted or predetermined. The alkaline proteases according to the present invention may include wild type enzymes, wild type variants or artificial variants.

The "another alkaline protease" may be a wild type enzyme or a wild type variant. In this context it is preferred that the alkaline protease has oxidant resistance and a molecular weight, as determined by SDS-PAGE, of 43,000±2,000. More preferred is an alkaline protease having an amino acid sequence that has at least 60% homology with the amino acid sequence of SEQ ID NO:1. Particularly preferred is an alkaline protease having an amino acid sequence that has at least 60% homology with the amino acid sequence of SEQ ID NO:1, has oxidant resistance, functions under alkaline conditions (pH 8 or greater), is stable with at least 80% residual activity when treated at pH 10 for 10 minutes even at 50° C., is inhibited by diisopropyl fluorophosphate (DFP) and phenylmethane sulfonyl fluoride (PMSF) and has a molecular weight, as determined by SDS-PAGE, of 43,000±2,000.

The term "having oxidant resistance" as used herein means that the alkaline protease has at least 50% of residual activity (synthetic substrate assay) when treated in a 50 mM hydrogen peroxide solution (containing 5 mM calcium chloride) at pH 10 (a 20 mM Britton-Robinson buffer) at 20° C. for 20 minutes.

Examples of the "alkaline protease having an amino acid sequence represented by SEQ ID NO:1" include KP43 [derived from Bacillus sp. strain KSM-KP43 (FERM BP-6532), WO99/18218], while those of the "alkaline protease having an amino acid sequence showing at least 60% homology with the amino acid sequence of SEQ ID NO:1" include protease KP9860 having an amino acid sequence represented by SEQ ID NO:2 [derived from Bacillus sp. strain KSM-KP9860 (FERM BP-6534), WO99/18218], Protease E-1 having an amino acid sequence represented by SEQ ID NO:3 [derived from Bacillus sp. strain No. D-6 (FERM P-1592), JP740710], Protease Ya having an amino acid sequence represented by SEQ ID NO:4 [derived from Bacillus sp. strain Y (FERM BP-1029), JP861210], Protease SD521 having an amino acid sequence represented by SEQ ID NO:5 [derived from Bacillus sp. strain SD-521 (FERM BP-11162), JP910821], Protease A-1 having an amino acid sequence represented by SEQ ID NO:6 (derived from NCIB12289, WO8801293), and Protease A-2 having an amino acid sequence represented by SEQ ID NO:7 (derived from NCIB12513, WO8801293). Of these, the amino acid sequences selected from SEQ ID NOS. 2 to 7 or alkaline proteases showing at least 80%, more preferably at least 90%, especially at least 95% homology therewith are preferred.

The homology of an amino acid sequence is calculated by Lipman-Pearson's method (Science, 227, 1435(1985)).

The "amino acid residue at a corresponding position" can be identified by comparing amino acid sequences by using known algorithm, for example, that of Lipman-Pearson. The position of the "amino acid residue at a corresponding position" in the sequence of each protease can be determined by aligning the amino acid sequence of the protease in such a manner. It is presumed that the corresponding position exists at the three-dimensionally same position in the amino acid sequence of SEQ ID NO:1 and the amino acid residue existing at the same position brings about similar effects for a specific function of the protease.

Described specifically, (a) the amino acid residue at position 84 of SEQ ID NO:1 is a lysine residue. By employing the above-described method, the amino acid residue at the position corresponding thereto can be identified as the lysine residue at position 83 of SEQ ID NO:3. This amino acid residue is preferably arginine.

(b) Although the amino acid residue at position 104 of SEQ ID NO:1 is a leucine residue, this amino acid residue or an amino acid residue corresponding thereto is preferably a proline residue.

(c) Although the amino acid residue at position 256 of SEQ ID NO:1 is a methionine residue, particularly preferred as this amino acid residue is an alanine, serine, glutamine, valine, leucine, asparagine, glutamic acid or aspartic acid residue.

(d) Although the amino acid residue at position 369 of SEQ ID NO:1 is an aspartic acid residue, this amino acid residue or amino acid residue corresponding thereto is preferably an asparagine residue.

(e) Although the amino acid residue at position 66 or 264 of SEQ ID NO:1 is an asparagine residue, this amino acid residue is preferably a glutamine, aspartic acid, serine, glutamic acid, alanine, threonine, leucine, methionine, cysteine, valine, glycine or isoleucine residue, with an aspartic acid, serine or glutamic acid residue being particularly preferred. More preferred is the case wherein the amino acid residue at position 66 is an aspartic acid residue and that at position 264 is a serine residue.

(f) Although the amino acid residue at each of positions 57, 101 to 106, 136, 193 and 342 of SEQ ID NO:1 is a glycine residue, this amino acid residue is preferably a lysine, serine, glutamine, phenylalanine, valine, arginine, tyrosine, leucine, isoleucine, threonine, methionine, cysteine, tryptophan, aspartic acid, glutamic acid, histidine, proline or alanine residue. Particularly preferred is the case wherein the amino acid residue at position 57, 136, 193 or 342 is an alanine residue, or that at position 103 is an arginine residue.

(g) Although the amino acid residue at position 46 or 205 of SEQ ID NO:1 is a phenylalanine residue, this amino acid residue is preferably a tyrosine, tryptophan, alanine, asparagine, glutamic acid, threonine, valine, leucine, isoleucine, histidine, serine, lysine, glutamine, methionine or cysteine residue. Particularly preferred is the case wherein the amino acid residue at position 46 is a leucine residue.

(h) Although the amino acid residue at position 54, 119, 138, 148 or 195 of SEQ ID NO:1 is a tyrosine residue, this amino acid residue is preferably a tryptophan, phenylalanine, alanine, asparagine, glutamic acid, threonine, valine, histidine, serine, glutamine, methionine, glycine, aspartic acid, proline, lysine, arginine or cysteine residue. Particularly preferred is the case wherein the amino acid residue at position 195 is an alanine, aspartic acid, glutamic acid, glutamine, valine, tryptophan, glycine, lysine, threonine, methionine, cysteine, phenylalanine, proline, serine, arginine, asparagine or histidine residue.

(i) Although the amino acid residue at position 247 of SEQ ID NO:1 is a lysine residue, this amino acid residue is preferably a tryptophan, phenylalanine, alanine, asparagine, glutamic acid, threonine, valine, leucine, isoleucine, histidine, serine, glutamine, methionine or cysteine residue. As the amino acid residue at position 247, an arginine or threonine residue is particularly preferred.

(j) Although the amino acid residue at position 124 of SEQ ID NO:1 is an arginine residue, this amino acid residue is preferably an alanine or lysine residue.

(k) Although the amino acid residue at position 107 of SEQ ID NO:1 is a leucine residue, this amino acid residue is preferably a lysine, arginine, alanine or serine residue, with a lysine residue being particularly preferred.

(l) Although the amino acid residue at position 257 of SEQ ID NO:1 is an alanine residue, this amino acid residue is preferably a valine or isoleucine residue, with a valine residue being particularly preferred.

With regards to "another alkali protease" which is preferred among the above-exemplified ones, positions corresponding to (a) to (d) and (e) to (l) of the amino acid sequence (SEQ ID NO:1) of Protease KP43 and specific examples of an amino acid residue are shown below (Table 1-a, Table 1-b).

TABLE 1-a

| | Proteases | | | | | | |
|---|---|---|---|---|---|---|---|
| | KP43 | 9860 | E-1 | Ya | SD-521 | A-1 | A-2 |
| Position | SEQ ID NO:1 | SEQ ID NO:2 | SEQ ID NO:3 | SEQ ID NO:4 | SEQ ID NO:5 | SEQ ID NO:6 | SEQ ID NO:7 |
| (a) | 84 Lys | 84 Lys | 83 Lys | 83 Lys | 83 Lys | 84 Lys | 83 Lys |
| (b) | 104 Leu | 104 Leu | 103 Leu | 103 Leu | 103 Leu | 104 Leu | 103 Leu |
| (c) | 256 Met | 256 Met | 255 Met | 255 Met | 255 Met | 256 Met | 255 Met |
| (d) | 369 Asr | 369 Asp | 368 Asp | 368 Asp | 368 Asp | 369 Asp | 368 Asp |

TABLE 1-b

| | Proteases | | | | | | |
|---|---|---|---|---|---|---|---|
| | KP43 | 9860 | E-1 | Ya | SD-521 | A-1 | A-2 |
| Position | SEQ ID NO:1 | SEQ ID NO:2 | SEQ ID NO:3 | SEQ ID NO:4 | SEQ ID NO:5 | SEQ ID NO:6 | SEQ ID NO:7 |
| (e) | 66 Asn | 66 Asn | 66 Asn | 66 Asn | 66 Asn | 66 Asn | 66 Asn |
| | 264 Asn | 264 Asn | 263 Asn | 263 Asn | 263 Asn | 264 Asn | 263 Asn |

TABLE 1-b-continued

| | Proteases | | | | | | |
|---|---|---|---|---|---|---|---|
| Posi-tion | KP43 SEQ ID NO:1 | 9860 SEQ ID NO:2 | E-1 SEQ ID NO:3 | Ya SEQ ID NO:4 | SD-521 SEQ ID NO:5 | A-1 SEQ ID NO:6 | A-2 SEQ ID NO:7 |
| (f) | 57 Gly | 57 Gly | 56 Gly | 56 Gly | 56 Gly | 57 Gly | 56 Gly |
| | 101 Gly | 101 Ser | 100 Ser | 100 Ser | 100 Ser | 101 Asn | 100 Gly |
| | 102 Gly | 102 Gly | 101 Gly | 101 Gly | 101 Gly | 102 Gly | 101 Gly |
| | 103 Gly | 103 Gly | 102 Gly | 102 Gly | 102 Gly | 103 Gly | 102 Gly |
| | 105 Gly | 105 Gly | 104 Gly | 104 Gly | 104 Gly | 105 Gly | 104 Gly |
| | 106 Gly | 106 Gly | 105 Gly | 105 Gly | 105 Gly | 106 Gly | 105 Gly |
| | 136 Gly | 136 Gly | 135 Gly | 135 Gly | 135 Gly | 136 Gly | 135 Gly |
| | 193 Gly | 193 Gly | 192 Gly | 192 Gly | 192 Gly | 193 Gly | 192 Gly |
| | 342 Gly | 342 Gly | 341 Gly | 341 Gly | 341 Gly | 342 Gly | 341 Gly |
| (g) | 46 Phe | 46 Phe | 46 Phe | 46 Phe | 46 Phe | 46 Phe | 46 Phe |
| | 205 Phe | 205 Phe | 204 Phe | 204 Phe | 204 Phe | 205 Phe | 204 Phe |
| (h) | 195 Tyr | 195 Tyr | 194 Ile | 194 Ile | 194 Leu | 195 Tyr | 194 Tyr |
| (i) | 247 Lys | 247 Lys | 246 Lys | 246 Lys | 246 Lys | 247 Lys | 246 Lys |
| (j) | 124 Arg | 124 Arg | 123 Arg | 123 Arg | 123 Arg | 124 Arg | 123 Arg |
| (k) | 107 Leu | 107 Leu | 106 Leu | 106 Leu | 106 Leu | 107 Leu | 106 Leu |
| (l) | 257 Ala | 257 Ala | 256 Ala | 256 Ala | 256 Ala | 257 Ala | 256 Ala |

In the alkaline proteases of the present invention, deletion of an amino acid residue or selection in (a) to (d) or (e) to (l) may be conducted at two or more positions simultaneously.

When the alkaline protease of the present invention is a variant, the "protease having an ammo acid sequence represented by SEQ ID NO:1" or the above-exemplified "another alkaline protease" serves as an alkaline protease prior to mutation (which may be called "parent alkaline protease"). By introducing a mutation to a desired site of this parent alkaline protease, the alkaline protease of the present invention may be obtained. For example, the alkaline protease of the present invention may be obtained by deleting or substituting, with another amino acid residue, the amino acid residue at a position selected from the above-described (a) to (d) and (e) to (l) of the amino acid sequence of SEQ ID NO:1 (Protease KP43) or at the corresponding position of the amino acid sequence of another alkaline protease. More specifically, the amino acid sequence of another alkaline protease may be an amino acid sequence represented by SEQ ID NOS:2 to 7.

The alkaline protease of the present invention can be obtained, for example, by introducing mutation to a cloned gene encoding a parent alkaline protease, transforming a proper host by using the resulting mutated gene and then culturing the recombinant host. Cloning of the gene for encoding a parent alkaline protease may be carried out using an ordinary gene recombination technique, for example, in accordance with the process as described in WO99/18218, JP901128 or WO98/56927.

For mutation of a gene encoding a parent alkaline protease, either one of random mutation or site-specific mutation which is prevalent now can be adopted. More specifically, mutation can be effected using, for example, "Site-Directed Mutagenesis System Mutan-Super Express Kit" of Takara Shuzo Co., Ltd. By using recombinant PCR (polymerase chain reaction) as described in "PCR protocols" (Academic Press, New York, 1990), a desired sequence of a gene can be replaced with a sequence of another gene corresponding to the desired sequence.

The following process may be employed for the production of the protease variant of the present invention by using the resulting mutated gene. A DNA encoding the protease variant of the present invention is stably amplified by linking the mutated gene with a DNA vector capable of amplifying the same. Alternatively, the DNA encoding the protease variant of the present invention is stably amplified by introducing the mutated gene onto a chromosomal DNA capable of maintaining it stably. Subsequent thereto, the gene is introduced into a host permitting stable and efficient expression of the gene, whereby the variant protease is produced. Hosts satisfying the above-described conditions include microorganisms belonging to Bacillus sp., Escherichia coli, mold, yeast and Actinomyces.

The alkaline protease of the present invention thus obtained has stable protease activity in an alkaline environment, is free from the inhibition of caseinolytic activity by higher fatty acids, and has a molecular weight, as determined by SDS-PAGE, of 43,000±2,000. For example, the protease variant available from, as a parent strain, the protease having an amino acid sequence of SEQ ID NO:1 has the below-described physicochemical properties.

(i) Acting pH Range

It acts in a wide pH range of from 4 to 13 and exhibits at least 80% of the optimum pH active value at pH 6 to 12.

(ii) Stable pH Range

It is stable within a pH range of 6 to 11 when treated at 40° C. for 30 minutes.

(iii) Influence of Fatty Acids

Its caseinolytic activity is not inhibited by oleic acid.

Such proteases of the present invention have excellent specific activity, oxidant resistance and detergency and are therefore useful as an enzyme to be incorporated in various detergent compositions. Particularly, the proteases wherein the amino acid residue at position (a) to (d) of SEQ ID NO:1 or at a position corresponding thereto has been deleted or specified are superior in detergency. Among them, those having, as the amino acid residue at (c) position 256 or at a position corresponding thereto, an alanine, serine, glutamine, valine, leucine, asparagine, glutamic acid or aspartic acid residue have both high specific activity and strong oxidant resistance. The proteases wherein the amino acid residue at position (e) to (l) of SEQ ID NO:1 or at a position corresponding thereto has been deleted or specified have particularly excellent specific activity.

The above-described protease may be added to the detergent composition of the present invention in an amount sufficient to permit exhibition of its activity. Although 0.1 to 5000 P.U. can be added per 1 kg of the detergent composition, 1000 P.U. or less, preferably 500 P.U. is added in consideration of economy.

To the detergent composition of the present invention, various enzymes can be used in combination with the alkaline protease of the present invention. Examples include hydrolases, oxidases, reductases, transferases, lyases, isomerases, ligases and synthetases. Of these, proteases, cellulases, lipases, keratinases, esterases, cutinases, amylases, pullulanases, pectinases, mannases, glucosidases, glucanases, cholesterol oxidases, peroxidases, laccases and proteases other than the alkaline protease used in the present invention are preferred.

Proteases include commercially available Alcalase, Esperase, Savinase and Everlase (each, product of Novo Nordisk), Properase and Purafect (each, product of Genencor International Inc.), and KAP (Kao Corp). Cellulases include Cellzyme and Carezyme (each, product of Novo Nordisk), KAC (Kao Corp.) and alkaline cellulase produced by Bacillus sp. strain KSM-S237 as described in Japanese Patent Application Laid-Open No. Hei 10-313859. Amylases include Termamyl and Duramyl (each, product of Novo Nordisk), Purastar (Genencor International Inc.), and KAM (Kao Corp.). Lipases include Lipolase and Liporase Ultra (each, product of Novo Nordisk). The above-exemplified enzyme may be incorporated in an amount of 0.001 to 10%, preferably 0.03 to 5%.

A surfactant may be incorporated in an amount of 0.5 to 60 wt. % (which will hereinafter be called "%", simply) in the detergent composition. To a powdery detergent composition and a liquid detergent composition, addition of 10 to 45% and 20 to 50% are preferred, respectively. When the detergent composition of the present invention is a bleaching detergent or automatic dishwasher detergent, the surfactant may usually be added in an amount of 1 to 10%, preferably 1 to 5%.

A divalent metal ion scavenger may be added in an amount of 0.01 to 50%, with 5 to 40% being preferred.

An alkali agent and inorganic salt may be added in an amount of 0.01 to 80%, preferably 1 to 40%.

An antisoil redeposition agent may be added in an amount of 0.001 to 10%, preferably 1 to 5%.

A bleaching agent (ex. hydrogen peroxide or percarbonate) is added preferably in an amount of 1 to 10%. Upon use of the bleaching agent, 0.01 to 10% of a bleaching activator can be added.

As a fluorescent brightener, biphenyl type ones (such as "Tinopal CBS-X") and stilbene type ones (such as DM fluorescent dye) can be used. It is added preferably in an amount of 0.001 to 2%.

The detergent composition of the present invention can be prepared in a conventional manner by using the alkaline protease obtained by the above-described process and the above-described known detergent components in combination. The detergent form can be selected according to the using purpose. Examples include liquid, powder and granule.

When the alkaline protease of the present invention is added to a powdery detergent composition, it is preferred to prepare detergent particles in advance. After preparation of the detergent particles, the alkaline protease granules are mixed therein in accordance with the process as described in Japanese Patent Application Laid-Open No. Sho 62-25790 to avoid the contact of workers or end users with the enzyme upon preparation or use of the detergent or to prevent heat-induced deactivation or decomposition the enzyme.

The detergent composition of the present invention thus available is usable as a laundry detergent, bleaching detergent, automatic dishwasher detergent, pipe cleaner and artificial tooth cleaner. Use as a laundry detergent, bleaching detergent or automatic dishwasher detergent is particularly preferred.

EXAMPLE 1

Mutation was introduced at random into a protease structural gene of about 2.0 kb including a termination codon by the following manner. First, PCR was conducted using a primer capable of amplifying this 2.0 kb. A PCR master mix contained 5 ng of a template DNA, 20 pmoL of a phosphorylated primer, 20 nmoL of each dNTP, 1 $\mu$moL of Tris/HCl (pH 8.3), 5 $\mu$moL of KCl, 0.15 $\mu$moL of $MgCl_2$ and 2.5 U TaqDNA polymerase, and its total amount was adjusted to 100 $\mu$L. After modification of the template by allowing it to stand at 94° C. for 5 minutes, PCR was performed for 30 cycles, each cycle consisting of treatment at 94° C. for 1 min, at 55° C. for 1 mm and at 72° C. for 1.5 min. The PCR product was purified by "PCR product purification Kit" (product of Boeringer Manheim), followed by elution in 100 $\mu$L of sterile water. With 1 $\mu$L of the eluate, second PCR was conducted under conditions similar to those of the first PCR except for the template DNA. After completion of the second PCR, the PCR product was purified in a similar manner to the first PCR, followed by elution in 100 $\mu$L of sterile water.

The amplified DNA fragment was integrated in a vector by polymerase reaction using "LATaq" produced by Takara Shuzo Co., Ltd. Described specifically, after addition of 5 $\mu$L of a buffer for LATaq (a 10-fold concentrate), 8 $\mu$L of a dNTP solution and 0.5 $\mu$L of LATaq DNA polymerase, and as a template, 20 ng of plasmid pHA64TS (having a protease structural gene linked with an expression vector pHA64) to 35 $\mu$L of the purified eluate, the total amount was adjusted to 50 $\mu$L. PCR reaction of the resulting liquid was carried out for 30 cycles, each consisting of treatment at 94° C. for 1 min, 55° C. for 1 min and 72° C. for 4 min. By the subsequent ethanol precipitation, the PCR product was collected. This PCR product had a shape of a plasmid having a nick at the 5' prime end of the primer. Ligase reaction by T4 ligase (product of Takara Shuzo Co., Ltd.) was conducted to link this nick portion.

By using 10 $\mu$L of this ligase reactiion mixture, transformation of the *Bacillus subtilis* strain ISW1214 was conduced, whereby about $4\times10^5$ transformants were obtained. The resulting transformants of the strain ISW1214 were cultured on a skin-milk-containing medium (containing 1% skim milk, 1% bactotrypton, 1% sodium chloride, 0.5% yeast extract, 1.5% agar and 7.5 $\mu$g/ml of tetracycline) and halo formation, which was presumed to reflect the protease secretion amount, was observed.

EXAMPLE 2

Purification of an Enzyme

The protease active fraction was prepared in the following manner. The transformants obtained in Example 1 was cultured at 30° C. for 60 hours on a medium A (3% polypeptone S (product of Nippon Pharmaceutical), 0.5% yeast extract, 1% fish meat extract (product of Wako Pure Chemical Industries, Ltd.), 0.15% dipotassium phosphate, 0.02% magnesium sulfate 7 hydrate, 4% maltose and 7.5 $\mu$g/mL of tetracycline). The supernatant of the thus-obtained cultured medium was added with ammonium sulfate to give 90% saturation, whereby salting-out of protein was caused. The sample obtained by salting-out was dissolved in a 10 mM tris HCl buffer (pH 7.5) containing 2 mM of calcium chloride. The resulting solution was dialyzed overnight against the same buffer by using a dialysis membrane. The fraction in the dialysis membrane was applied to DEAE Bio-Gel A (product of Bio-Rad Laboratories) equilibrated with a 10 mM his HCl buffer (pH 7.5) containing 2 mM calcium chloride to collect the protease active fraction not adsorbed to the ion-exchanger. This active fraction was applied further to "SP-Toyopearl 550W" (product of Tosob Corp.) equilibrated with the same buffer, followed by elution with a 0 to 50 mM sodium chloride solution, whereby a protease active fraction was obtained. The resulting fraction was analyzed by SDS-PAGE electrophoresis to confirm that the protease was obtained as substantially uniform protein. The protein concentration was measured in accordance with the method of Lowry, et al. (J. Biol. Chem. 193, 265–275 (1981)) by using bovine serum albumin (product of Bio-Rad Laboratories) as a standard.

EXAMPLE 3

Measuring Method of Protease Activity (1) Synthetic Substrate Assay

A decomposition rate was measured using a synthetic peptide made of Glt-Ala-Ala-Pro-Leu(A-A-P-L) as a substrate. Described specifically, a 50 mM borate/KCl buffer (pH 10.5) containing each enzyme to be evaluated and 3 mM of Glt-A-A-P-L-pNA (product of Peptide Institute, Inc) was kept at 30° C. for 10 minutes and then, an absorbance at 420 nm was periodically measured. The peptide hydrolyzing activity was determined from an increasing ratio of the absorbance at 420 nm per unit hour. The protein was determined using a protein assay kit of Bio-Rad Laboratories.

(2) Natural Substrate Assay

After 1.0 mL of a 50 mM borate buffer (pH 10) containing 1% (w/v) of casein was kept at 30° C. for 5 minutes, 0.1 mL of an enzyme solution was added and reaction was conducted for 15 minutes. To the reaction mixture, 2.0 mL of a reaction-stopping solution (0.11M trichloroacetic acid—0.22M sodium acetate—0.33M acetic acid) was added. The resulting mixture was allowed to stand at room temperature for 30 minutes and the filtered. The acid soluble protein in the filtrate was quantitatively determined by the modified method of Lowery, et al. Described specifically, after addition of 2.5 mL of an alkaline copper solution [1% potassium sodium tartrate: 1% copper sulfate: 1% sodium carbonate= 1:1:100] to the filtrate, the resulting solution was allowed to stand at room temperature for 10 minutes. Then, 0.25 mL of a diluted phenol solution (a phenol reagent (product of Kanto Kagaku) diluted 2-fold with ion exchange water) was added. After the resulting mixture was kept at 30° C. for 30 minutes, absorbance at 660 nm was measured. One enzyme unit was designated as a quantity of the enzyme for liberating the acid soluble protein hydrolysis product corresponding to 1 mmol of tyrosine for 1 min in the above-described reaction.

EXAMPLE 4

(1) Preparation of Granular Detergent

Detergency of the detergent as described in Example 3 of WO99/29830 was evaluated. Described specifically, 465 kg of water was poured in a mixing tank of 1 m$^3$ equipped with a stirring blade. After its water temperature reached 55° C., 48 kg of a 50% (w/v) aqueous solution of sodium dodecylenzenesulfonate and 135 kg of a 40% (w/v) aqueous solution of sodium polyacrylate were added. After stirring for 15 minutes, 120 kg of sodium carbonate, 60 kg of sodium sulfate, 9 kg of sodium sulfite and 3 kg of a fluorescent dye were added. After stirring for further 15 minutes, 300 kg of zeolite was added. The mixture was stirred for 30 minutes to yield a uniform slurry (the slurry had a water content of 50 wt. %). By spraying this slurry from a pressure spraying nozzle disposed in the vicinity of the top of a spray drying tower, base granules were obtained (a high temperature gas was fed to the spray drying tower at 225° C. from the tower bottom and discharged from the tower top at 105° C.).

Then, 15 parts by weight of a nonionic surfactant, 15 parts by weight of a 50 wt. % aqueous solution of sodium dodecylbenzenesulfonate and 1 part by weight of polyethylene glycol were mixed under heating to 70° C., whereby a mixture was obtained. In a Loedige mixer (product of Matsuzaka Giken Co., Ltd., capacity: 20L, equipped with a jacket), 100 parts by weight of the base granules obtained above were charged and stirring by a main shaft (150 rpm) and chopper (4000 rpm) was started. Warm water of 75° C. was caused to flow in the jacket at 10 L/min, the mixture was charged therein in 3 minutes, and then stirring was conducted for 5 minutes. The surface of the detergent particles were covered with 10 parts by weight of crystalline aluminosilicate, whereby the final product of the granular detergent was obtained.

Raw Materials Used

Aqueous solution of sodium dodecylbenzenesulfonate: "Neopelex F65" (product of Kao Corp.)

Nonionic surfactant: "Emulgen 108KM" (product of Kao) added with 8.5 moles, on average, of ethylene oxide Aqueous solution of sodium polyacrylate: having an average molecular weight of 10000 (prepared in accordance with the process as described in Example of Japanese Patent Publication No. Hei 2-24283)

Sodium carbonate: dense ash (product of Central Glass Co., Ltd.)

Zeolite: "Zeolite 4A" having an average particle size of 3.5 im (product of Tosoh Corp)

Polyethylene glycol: "K-PEG6000" (average molecular weight of 8500, product of Kao Corp.)

Fluorescent dye: "Tinopal CBS-X" (product of Ciba Geigy)

(2) Preparation of Granulated Protease

From the alkaline proteases of the present invention and a purified preparation of a parent alkaline protease, granulated protease was prepared based on the process as described in Japanese Patent Application Laid-Open No. Sho 62-257990 (6P.U./g)

(3) Measurement of Detergency

In 1L of an aqueous calcium solution (71.2 mg calcium carbonate/1L) adjusted to 20° C., 0.67 g of each of the detergent compositions as shown in Table 2 was dissolved. With the resulting solution, a test cloth ("EMPA117" (prepared by Swiss Federal Laboratories for Materials Testing and Research, blood/milk/carbon) cut into a piece of 6×6 cm was washed using a Terg-O-tometer (product of Ueshima Seisakusho) at 20° C. and 100 rpm for 10 minutes. After rinsing and drying, the brightness was measured using a spectrophotometer ("CM3500d", product of MINOLTA). A detergency was calculated based on the below-described equation. The results are shown in Table 2.

$$\text{Detergency (\%)} = \frac{\text{Brightness of the test fabric after washing} - \text{that before washing}}{\text{Brightness of the test fabric before soiling} - \text{that before washing}} \times 100$$

Measuring results of the detergency of the protease variants obtained in Example 1 are shown in FIG. 1. The alkaline protease variants of the present invention each exhibited superior detergency to wild type enzymes to which mutation had not been introduced.

TABLE 2

|  |  | Invention products |  |  |  |  | Comparative products |  |
|---|---|---|---|---|---|---|---|---|
|  |  | 1 | 2 | 3 | 4 | 5 | 1 | 2 |
| Parts by weight | | | | | | | | |
| Granulated alkaline proteases of this invention | K84R | 0.5 | | | | | | |
| | L104P | | 0.5 | | | | | |
| | M256S | | | 0.5 | | | | |
| | M256A | | | | 0.05 | | | |
| | D369N | | | | | 0.5 | | |
| Granulated parent alkaline protease | | | | | | | 0.5 | |
| Granular detergent | | | | 99.5 | | | | 100 |
| Detergency (%) | | 38 | 38 | 36 | 36 | 34 | 31 | 23 |

EXAMPLE 5

Figure 2:
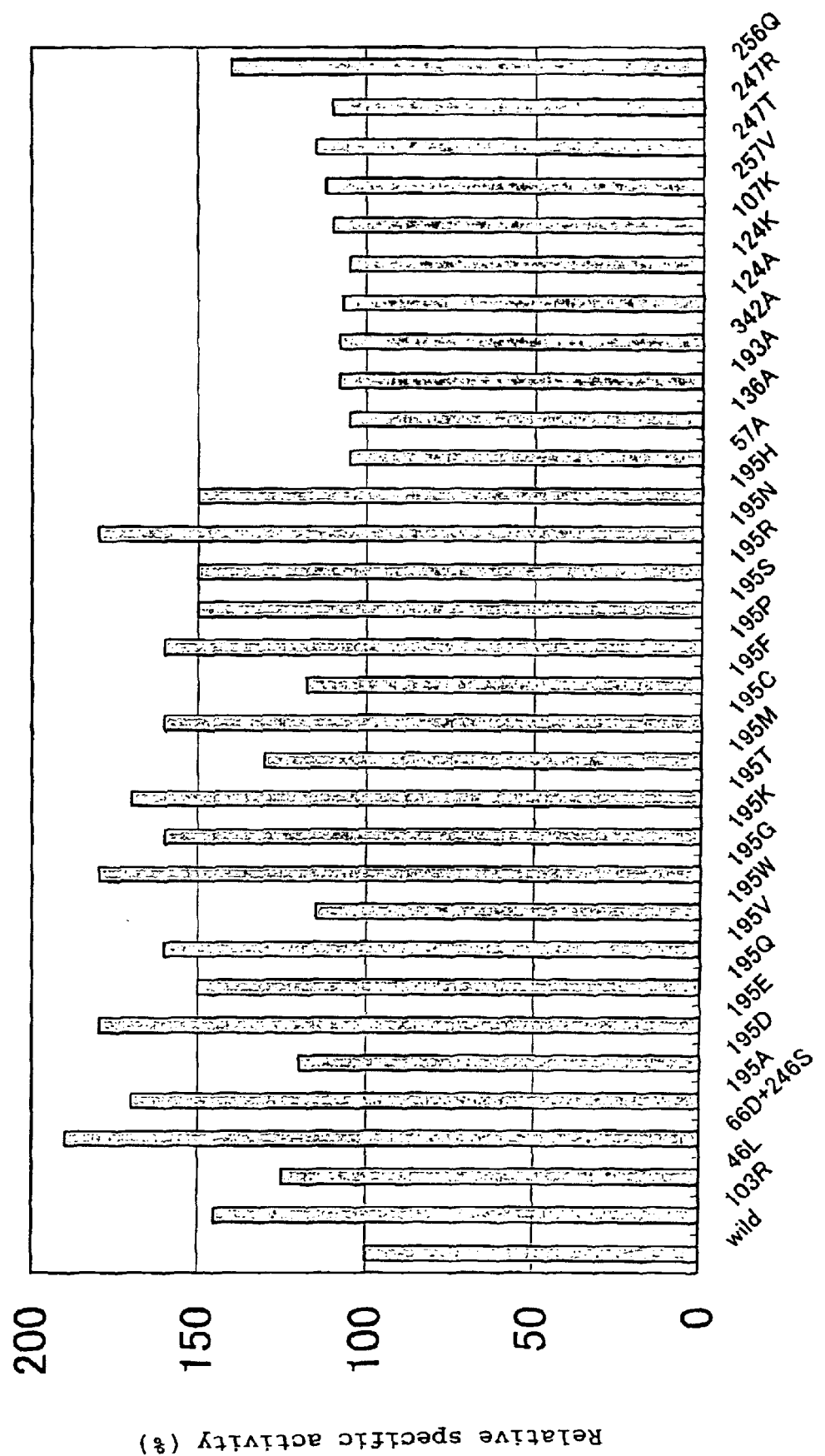
FIG. 2 is a diagram illustrating relative specific activity of each alkaline protease variant as described in Example 5.

Measuring results, in accordance with the synthetic substrate assay or natural substrate assay, of protease activity of the protease variants obtained in Example 1 (the proteases modified at 195-position and 256-position amino acid residues, respectively was measured by the latter assay, while the other proteases were measured by the former assay) are shown in FIG. 2. The alkaline protease variants of the present invention exhibited high specific activity.

EXAMPLE 6

Figure 3:
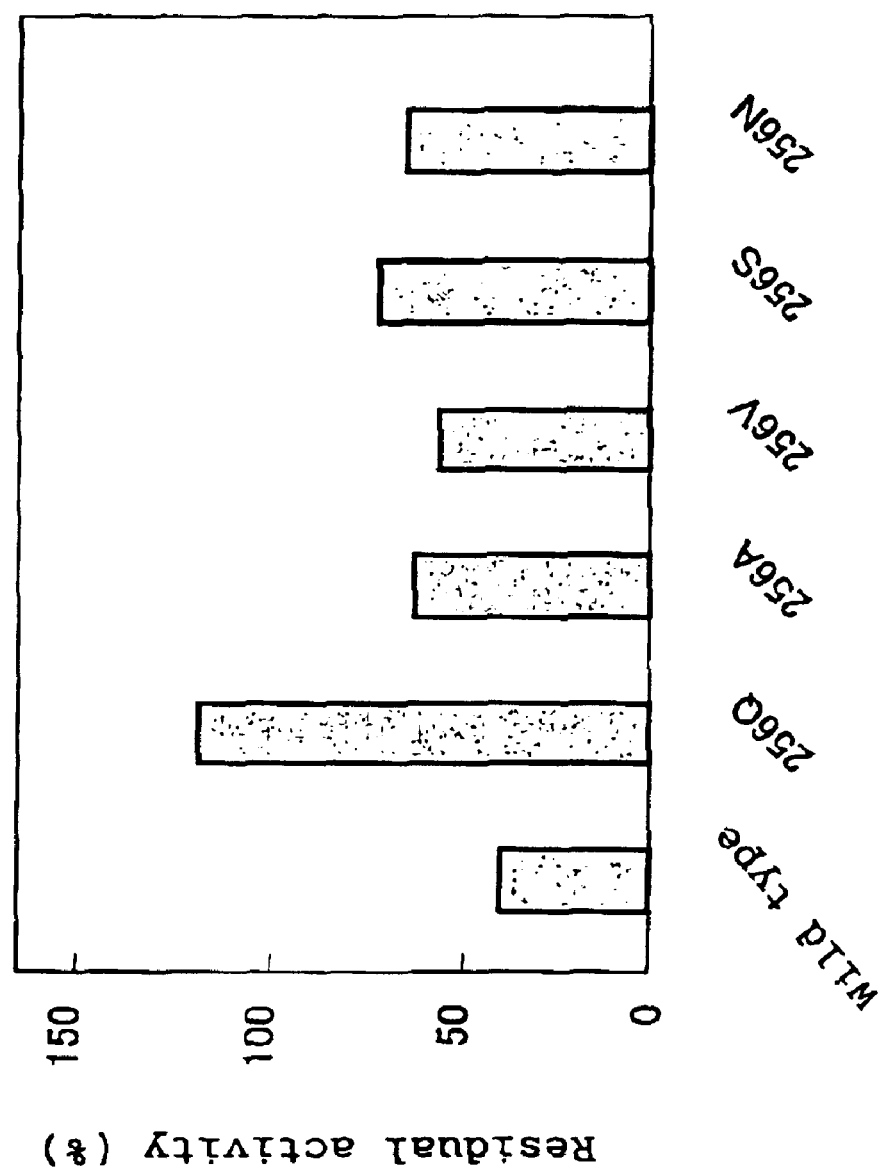
FIG. 3 is a diagram illustrating relative residual activity of a series of alkaline protease variants, in which position 256 of KP43 has been mutated, after treatment with an oxidant.

In 2 mL of a 100 mM borate buffer (pH 10.5) containing 3% of aqueous hydrogen peroxide, a 50 μL portion of each of the protease variants obtained by purification in Example 1 was added. The resulting mixture was allowed to stand at 30° C. for 30 minutes. After addition of an adequate amount of catalase (product of Boehringer Manheim) to remove excess hydrogen peroxide, the residual protease activity was measured by the synthetic substrate assay. In FIG. 3, the residual activity after treatment with aqueous hydrogen peroxide is shown relative to the activity before treatment set at 100%.

The alkaline protease variants of the present invention exhibited higher oxidant resistance than the parent alkaline protease.

INDUSTRIAL APPLICABILITY

The present invention makes it possible to provide alkaline proteases having activity even under a high concentration of fatty acids, having high specific activity, oxidant resistance and detergency, and being useful as an enzyme to be incorporated in a detergent.

What is claimed is:

1. An alkaline protease, comprising the amino acid sequence of SEQ ID NO:1 wherein one or more amino acid residues selected from the group consisting of
   (a) K84 is replaced with R;
   (b) L104 is replaced with P;
   (c) M256 is replaced with an amino acid selected from the group consisting of A, S, Q, V, L, N, E, and D; and
   (d) D369 is replaced with N.

2. An alkaline protease, comprising an amino acid sequence having at least 95% homology to the amino acid sequence represented by SEQ ID NO:1, wherein one or more amino acid residues selected from the group consisting of
   (a) K84 is replaced with R;
   (b) L104 is replaced with P;
   (c) M256 is replaced with an amino acid selected from the group consisting of A, S, Q, V, L, N, E, and D; and
   (d) D369 is replaced with N,
   wherein said alkaline protease has oxidant resistance, is active at an alkaline pH, and retains at least 80% residual activity when treated at pH 10 for 10 minutes.

3. An alkaline protease, comprising the amino acid sequence of SEQ ID NO: 1 wherein one or more amino acid residues selected from the group consisting of
   (a) N66 is replaced with an amino acid selected from the group consisting of Q, D, S, E, A, T, L, M, C, V, G, and I;
   (b) N264 is replaced with an amino acid selected from the group consisting of Q, D, S, E, A, T, M, C, V, G, and I;
   (c) G57 is replaced with an amino acid selected from the group consisting of K, S, Q, F, V, R, Y, L, I, T, M, C, W, D, E, H, P, and A;
   (d) G101 is replaced with an amino acid selected from the group consisting of K, S, Q, F, V, R, Y, L, I, T, M, C, W, D, E, H, P, and A;
   (e) G102 is replaced with an amino acid selected from the group consisting of K, S, Q, F, V, R, Y, L, I, T, M, C, W, D, E, H, P, and A;
   (f) G103 is replaced with an amino acid selected from the group consisting of K, S, Q, F, V, R, Y, L, I, T, M, C, W, D, E, H, P, and A;
   (g) L104 is replaced with an amino acid selected from the group consisting of K, S, Q, F, V, R, Y, I, T, M, C, W, D, E, H, P, and A;
   (h) G105 is replaced with an amino acid selected from the group consisting of K, S, Q, F, V, R, Y, L, T, M, C, W, D, E, H, P, and A;
   (i) G106 is replaced with an amino acid selected from the group consisting of K, S, Q, F, V, R, Y, L, I, T, M, C, W, D, E, H, P, and A;
   (j) G136 is replaced with an amino acid selected from the group consisting of K, S, Q, F, V, R, Y, L, T, M, C, W, D, E, H, P and A;
   (k) G193 is replaced with an amino acid selected from the group consisting of K, S, O, F, V, R, Y, L, I, T, M, C, W, D, E, H, P, and A;
   (l) G342 is replaced with an amino acid selected from the group consisting of K, S, Q, F, V, R, Y, L, I, T, M, C, W, D, E, H, P, and A;
   (m) F46 is replaced with an amino acid selected from the group consisting of Y, W, A, N, E, T, V, L, I, H, S, K, Q, M, and C;
   (n) F205 is replaced with an amino acid selected from the group consisting of Y, W, A, N, E, T, V, L, I, H, S, K, Q, M, and C;
   (o) Y54 is replaced with an amino acid selected from the group consisting of W, F, A, N, E, T, V, H, S, K, Q, M, G, D, P, R, and C;
   (p) Y119 is replaced with an amino acid selected from the group consisting of W, F, A, N, E, T, V, H, S, K, Q, M, G, D, P, R, and C;
   (q) Y138 is replaced with an amino acid selected from the group consisting of W, F, A, N, E, T, V, H, S, K, Q, M, G, D, P, R, and C;

(r) Y148 is replaced with an amino acid selected from the group consisting of W, F, A, N, E, T, V, H, S, K, Q, M, G, D, P, R, and C;

(s) Y195 is replaced with an amino acid selected from the group consisting of W, F, A, N, E, T, V, H, S, K, Q, M, G, D, P, R, and C;

(t) K247 is replaced with an amino acid selected from the group consisting of W, F, A, N, E, T, V, L, I, H, S, Q, M, and C;

(u) R124 is replaced with an amino acid selected from the group consisting of A and K;

(v) L107 is replaced with an amino acid selected from the group consisting of K, R, A, and S; and (w) A257 is replaced with an amino acid selected from the group consisting of V and I.

4. An alkaline protease, comprising an amino acid sequence having at least 95% homology to the amino acid sequence represented by SEQ ID NO:1, wherein one or more amino acid residues selected from the group consisting of (a) N66 is replaced with an amino acid selected from the group consisting of Q, D, S, E, A, T, L, M, C, V, G, and I;

(b) N264 is replaced with an amino acid selected from the group consisting of Q, D, S, E, A, T, L, M, C, V, G, and I;

(c) G57 is replaced with an amino acid selected from the group consisting of K, S, Q, F, V, R, Y, L, I, T, M, C, W, D, E, H, P, and A;

(d) G101 is replaced with an amino acid selected from the group consisting of K, S, Q, F, V, R, Y, L, I, T, M, C, W, D, E, H, P, and A;

(e) G102 is replaced with an amino acid selected from the group consisting of K, S, Q, F, V, R, Y, L, I, T, M, C, W, D, E, H, P, and A;

(f) G103 is replaced with an amino acid selected from the group consisting of K, S, Q, F, V, R, Y, L, I, T, M, C, W, D, E, H, P, and A;

(g) L104 is replaced with an amino acid selected from the group consisting of K, S, Q, F, V, R, Y, I, T, M, C, W, D, E, H, P, and A;

(h) G105 is replaced with an amino acid selected from the group consisting of K, S, Q, F, V, R, Y, L, I, T, M, C, W, D, E, H, P, and A;

(i) G106 is replaced with an amino acid selected from the group consisting of K, S, Q, F, V, R, Y, L, I, T, M, C, W, D, E, H, P, and A;

(j) G136 is replaced with an amino acid selected from the group consisting of K, S, Q, F, V, R, Y, L, I, T, M, C, W, D, E, H, P, and A;

(k) G193 is replaced with an amino acid selected from the group consisting of K, S, Q, F, V, R, Y, L, I, T, M, C, W, D, E, H, P, and A;

(l) G342 is replaced with an amino acid selected from the group consisting of K, S, Q, F, V, R, Y, L, I, T, M, C, W, D, E, H, P, and A;

(m) F46 is replaced with an amino acid selected from the group consisting of Y, W, A, N, E, T, V, L, I, H, S, K, Q, M, and C;

(n) F205 is replaced with an amino acid selected from the group consisting of Y, W, A, N, E, T, V, L, I, H, S, K, Q, M, and C;

(o) Y54 is replaced with an amino acid selected from the group consisting of W, F, A, N, E, T, V, H, S, K, Q, M, G, D, P, R, and C;

(p) Y119 is replaced with an amino acid selected from the group consisting of W, F, A, N, E, T, V, H, S, K, Q, M, G, D, P, R, and C;

(q) Y138 is replaced with an amino acid selected from the group consisting of W, F, A, N, E, T, V, H, S, K, Q, M, G, D, P, R, and C;

(r) Y148 is replaced with an amino acid selected from the group consisting of W, F, A, N, E, T, V, H, S, K, Q, M, G, D, P, R, and C;

(s) Y195 is replaced with an amino acid selected from the group consisting of W, F, A, N, E, T, V, H, S, K, Q, M, G, D, P, R, and C;

(t) K247 is replaced with an amino acid selected from the group consisting of W, F, A, N, E, T, V, L, I, H, S, Q, M, and C;

(u) R124 is replaced with an amino acid selected from the group consisting of A and K;

(v) L107 is replaced with an amino acid selected from the group consisting of K, R, A, and S; and (w) A257 is replaced with an amino acid selected from the group consisting of V and I.

5. A detergent composition, comprising the alkaline protease according to claim 1.

6. A detergent composition comprising the alkaline protease according to claim 2.

7. A detergent composition comprising the alkaline protease according to claim 3.

8. A detergent composition comprising the alkaline protease according to claim 4.

9. The alkaline protease according to claim 1, wherein (d) D369 is replaced with N.

10. The alkaline protease according to claim 9, wherein one or more amino acid residues selected from the group consisting of (a) K84 is replaced with R;

(b) L104 is replaced with P; and (c) M256 is replaced with an amino acid selected from the group consisting of A, S, Q, V, L, N, E, and D.

11. The alkaline protease according to claim 2, wherein (d) D369 is replaced with N.

12. The alkaline protease according to claim 11, wherein one or more amino acid residues selected from the group consisting of (a) K84 is replaced with R;

(b) L104 is replaced with P; and (c) M256 is replaced with an amino acid selected from the group consisting of A, S, Q, V, L, N, E, and D.

* * * * *

UNITED STATES PATENT AND TRADEMARK OFFICE
CERTIFICATE OF CORRECTION

PATENT NO. : 6,803,222 B2
DATED : October 12, 2004
INVENTOR(S) : Yuji Hatada et al.

It is certified that error appears in the above-identified patent and that said Letters Patent is hereby corrected as shown below:

Column 29,
Line 60, "Q, D, S, E, A, T, M, C, V, G" should read -- Q, D, S, E, A, T, L, M, C, V, G, --

Signed and Sealed this

First Day of February, 2005

JON W. DUDAS
*Director of the United States Patent and Trademark Office*

SEQUENCE LISTING

<160> NUMBER OF SEQ ID NOS: 7

<210> SEQ ID NO 1
<211> LENGTH: 434
<212> TYPE: PRT
<213> ORGANISM: Bacillus sp.

<400> SEQUENCE: 1

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255
```

-continued

```
Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Gln Tyr Val Gly Asn Asp
    370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn
```

<210> SEQ ID NO 2
<211> LENGTH: 434
<212> TYPE: PRT
<213> ORGANISM: Bacillus sp.

<400> SEQUENCE: 2

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ala Thr Asn Lys Gly Met Ala Pro Gln Ala Asn Leu Val Phe Gln Ser
                85                  90                  95

Ile Met Asp Ser Ser Gly Leu Gly Gly Leu Pro Ser Asn Leu Gln
            100                 105                 110

Thr Leu Phe Ser Gln Ala Phe Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190
```

```
Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
        210                 215                 220

Thr Tyr Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
        260                 265                 270

Val Lys Asn Arg Gly Ile Thr Pro Lys Pro Ser Leu Leu Lys Ala Ala
        275                 280                 285

Leu Ile Ala Gly Ala Ala Asp Val Gly Leu Gly Tyr Pro Asn Gly Asn
        290                 295                 300

Gln Gly Trp Gly Arg Val Thr Leu Asp Lys Ser Leu Asn Val Ala Tyr
305                 310                 315                 320

Val Asn Glu Ser Ser Ala Leu Ser Thr Ser Gln Lys Ala Thr Tyr Thr
                325                 330                 335

Phe Thr Ala Thr Ala Gly Lys Pro Leu Lys Ile Ser Leu Val Trp Ser
        340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Arg Tyr Val Gly Asn Asp
370                 375                 380

Phe Ser Ala Pro Phe Asp Asn Asn Trp Asp Gly Arg Asn Asn Val Glu
385                 390                 395                 400

Asn Val Phe Ile Asn Ser Pro Gln Ser Gly Thr Tyr Thr Ile Glu Val
                405                 410                 415

Gln Ala Tyr Asn Val Pro Val Gly Pro Gln Asn Phe Ser Leu Ala Ile
        420                 425                 430

Val Asn

<210> SEQ ID NO 3
<211> LENGTH: 433
<212> TYPE: PRT
<213> ORGANISM: Bacillus sp.

<400> SEQUENCE: 3

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
                20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
        50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Gly Leu Pro Ser Asn Leu Asn Thr
                100                 105                 110

Leu Phe Ser Gln Ala Trp Asn Ala Gly Ala Arg Ile His Thr Asn Ser
        115                 120                 125
```

```
Trp Gly Ala Pro Val Asn Gly Ala Tyr Thr Ala Asn Ser Arg Gln Val
130                 135                 140

Asp Glu Tyr Val Arg Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
                180                 185                 190

Ser Ile Ala Asp Asn Pro Asn His Ile Ala Gln Phe Ser Arg Gly
                195                 200                 205

Ala Thr Arg Asp Gly Arg Ile Lys Pro Asp Val Thr Ala Pro Gly Thr
                210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
                260                 265                 270

Lys Asn Arg Gly Ile Thr Pro Lys Pro Ser Leu Ile Lys Ala Ala Leu
                275                 280                 285

Ile Ala Gly Ala Thr Asp Val Gly Leu Gly Tyr Pro Ser Gly Asp Gln
                290                 295                 300

Gly Trp Gly Arg Val Thr Leu Asp Lys Ser Leu Asn Val Ala Tyr Val
305                 310                 315                 320

Asn Glu Ala Thr Ala Leu Thr Thr Gly Gln Lys Ala Thr Tyr Ser Phe
                325                 330                 335

Gln Thr Gln Ala Gly Lys Pro Leu Lys Ile Ser Leu Val Trp Thr Asp
                340                 345                 350

Ala Pro Gly Ser Thr Thr Ala Ser Tyr Thr Leu Val Asn Asp Leu Asp
                355                 360                 365

Leu Val Ile Thr Ala Pro Asn Gly Gln Lys Tyr Val Gly Asn Asp Phe
                370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
                420                 425                 430

His
```

<210> SEQ ID NO 4
<211> LENGTH: 433
<212> TYPE: PRT
<213> ORGANISM: Bacillus sp.

<400> SEQUENCE: 4

```
Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
                20                  25                  30

Leu Asp Thr Gly Arg Asn Asp Ser Ser Met His Glu Ala Phe Arg Gly
                35                  40                  45

Lys Ile Thr Ala Leu Tyr Ala Leu Gly Arg Thr Asn Asn Ala Ser Asp
                50                  55                  60
```

```
Pro Asn Gly His Gly Thr His Val Ala Gly Ser Val Leu Gly Asn Ala
 65                  70                  75                  80

Leu Asn Lys Gly Met Ala Pro Gln Ala Asn Leu Val Phe Gln Ser Ile
             85                  90                  95

Met Asp Ser Ser Gly Leu Gly Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Asn Gly Asp Gln
    290                 295                 300

Gly Trp Gly Arg Val Thr Leu Asn Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Ile Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 5
<211> LENGTH: 433
<212> TYPE: PRT
<213> ORGANISM: Bacillus sp.
```

<400> SEQUENCE: 5

```
Asn Asp Val Ala Arg Gly Ile Val Lys Ala Asp Val Ala Gln Asn Asn
1               5                   10                  15
Tyr Gly Leu Tyr Gly Gln Gly Gln Val Val Ala Val Ala Asp Thr Gly
            20                  25                  30
Leu Asp Thr Gly Arg Asn Asp Ser Ser Met His Glu Ala Phe Arg Gly
        35                  40                  45
Lys Ile Thr Ala Leu Tyr Ala Leu Gly Arg Thr Asn Asn Ala Asn Asp
    50                  55                  60
Pro Asn Gly His Gly Thr His Val Ala Gly Ser Val Leu Gly Asn Ala
65                  70                  75                  80
Leu Asn Lys Gly Met Ala Pro Gln Ala Asn Leu Val Phe Gln Ser Ile
                85                  90                  95
Met Asp Ser Ser Gly Gly Leu Gly Gly Leu Pro Ser Asn Leu Asn Thr
            100                 105                 110
Leu Phe Ser Gln Ala Trp Asn Ala Gly Ala Arg Ile His Thr Asn Ser
        115                 120                 125
Trp Gly Ala Pro Val Asn Gly Ala Tyr Thr Ala Asn Ser Arg Gln Val
130                 135                 140
Asp Glu Tyr Val Arg Asn Asn Asp Met Thr Val Leu Phe Ala Ala Gly
145                 150                 155                 160
Asn Glu Gly Pro Asn Ser Gly Thr Ile Ser Ala Pro Gly Thr Ala Lys
                165                 170                 175
Asn Ala Ile Thr Val Gly Ala Thr Glu Asn Tyr Arg Pro Ser Phe Gly
            180                 185                 190
Ser Leu Ala Asp Asn Pro Asn His Ile Ala Gln Phe Ser Ser Arg Gly
        195                 200                 205
Ala Thr Arg Asp Gly Arg Ile Lys Pro Asp Val Thr Ala Pro Gly Thr
    210                 215                 220
Phe Ile Leu Ser Ala Arg Ser Ser Leu Ala Pro Asp Ser Ser Phe Trp
225                 230                 235                 240
Ala Asn Tyr Asn Ser Lys Tyr Ala Tyr Met Gly Gly Thr Ser Met Ala
                245                 250                 255
Thr Pro Ile Val Ala Gly Asn Val Ala Gln Leu Arg Glu His Phe Ile
            260                 265                 270
Lys Asn Arg Gly Ile Thr Pro Lys Pro Ser Leu Ile Lys Ala Ala Leu
        275                 280                 285
Ile Ala Gly Ala Thr Asp Val Gly Leu Gly Tyr Pro Ser Gly Asp Gln
    290                 295                 300
Gly Trp Gly Arg Val Thr Leu Asp Lys Ser Leu Asn Val Ala Tyr Val
305                 310                 315                 320
Asn Glu Ala Thr Ala Leu Ala Thr Gly Gln Lys Ala Thr Tyr Ser Phe
                325                 330                 335
Gln Ala Gln Ala Gly Lys Pro Leu Lys Ile Ser Leu Val Trp Thr Asp
            340                 345                 350
Ala Pro Gly Ser Thr Thr Ala Ser Tyr Thr Leu Val Asn Asp Leu Asp
        355                 360                 365
Leu Val Ile Thr Ala Pro Asn Gly Gln Lys Tyr Val Gly Asn Asp Phe
    370                 375                 380
Ser Tyr Pro Tyr Asp Asn Asn Trp Asp Gly Arg Asn Asn Val Glu Asn
385                 390                 395                 400
Val Phe Ile Asn Ala Pro Gln Ser Gly Thr Tyr Thr Ile Glu Val Gln
                405                 410                 415
```

```
Ala Tyr Asn Val Pro Ser Gly Pro Gln Arg Phe Ser Leu Ala Ile Val
            420                 425                 430
His
```

<210> SEQ ID NO 6
<211> LENGTH: 434
<212> TYPE: PRT
<213> ORGANISM: Bacillus sp.

<400> SEQUENCE: 6

```
Asn Asp Val Ala Arg Gly Ile Val Lys Ala Asp Val Ala Gln Ser Ser
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Ile Tyr Ala Leu Gly Arg Thr Asn Asn Ala Asn Asp
    50                  55                  60

Pro Asn Gly His Gly Thr His Val Ala Gly Ser Val Leu Gly Asn Gly
65                  70                  75                  80

Thr Ser Asn Lys Gly Met Ala Pro Gln Ala Asn Leu Val Phe Gln Ser
                85                  90                  95

Val Met Asp Ser Asn Gly Gly Leu Gly Gly Leu Pro Ser Asn Val Ser
            100                 105                 110

Thr Leu Phe Ser Gln Ala Tyr Ser Ala Gly Ala Arg Ile His Thr Asn
        115                 120                 125

Ser Trp Gly Ala Pro Val Asn Gly Ala Tyr Thr Thr Asp Ser Arg Asn
    130                 135                 140

Val Asp Asp Tyr Val Arg Lys Asn Asp Met Ala Val Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Thr Asp Ile Gly Leu Gly Tyr Pro Ser Gly Asn
    290                 295                 300

Gln Gly Trp Gly Arg Val Thr Leu Asp Lys Ser Leu Asn Val Ala Phe
305                 310                 315                 320

Val Asn Glu Thr Ser Ser Leu Ser Thr Asn Gln Lys Ala Thr Tyr Ser
                325                 330                 335

Phe Thr Ala Gln Ser Gly Lys Pro Leu Lys Ile Ser Leu Val Trp Ser
            340                 345                 350
```

```
Asp Ala Pro Ala Ser Thr Ser Ala Ser Val Thr Leu Val Asn Asp Leu
        355                 360                 365

Asp Leu Val Ile Thr Ala Pro Asn Gly Thr Lys Tyr Val Gly Asn Asp
    370                 375                 380

Phe Thr Ala Pro Tyr Asp Asn Asn Trp Asp Gly Arg Asn Asn Val Glu
385                 390                 395                 400

Asn Val Phe Ile Asn Ala Pro Gln Ser Gly Thr Tyr Thr Val Glu Val
                405                 410                 415

Gln Ala Tyr Asn Val Pro Gln Gly Pro Gln Ala Phe Ser Leu Ala Ile
            420                 425                 430

Val Asn

<210> SEQ ID NO 7
<211> LENGTH: 433
<212> TYPE: PRT
<213> ORGANISM: Bacillus sp.

<400> SEQUENCE: 7

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Ala
65                  70                  75                  80

Thr Asn Lys Gly Met Ala Pro Gln Ala Asn Leu Val Phe Gln Ser Ile
                85                  90                  95

Met Asp Ser Gly Gly Gly Leu Gly Gly Leu Pro Ala Asn Leu Gln Thr
            100                 105                 110

Leu Phe Ser Gln Ala Tyr Ser Ala Gly Ala Arg Ile His Thr Asn Ser
        115                 120                 125

Trp Gly Ala Pro Val Asn Gly Ala Tyr Thr Thr Asp Ser Arg Asn Val
    130                 135                 140

Asp Asp Tyr Val Arg Lys Asn Asp Met Thr Ile Leu Phe Ala Ala Gly
145                 150                 155                 160

Asn Glu Gly Pro Gly Ser Gly Thr Ile Ser Ala Pro Gly Thr Ala Lys
                165                 170                 175

Asn Ala Ile Thr Val Gly Ala Thr Glu Asn Leu Arg Pro Ser Phe Gly
            180                 185                 190

Ser Tyr Ala Asp Asn Ile Asn His Val Ala Gln Phe Ser Ser Arg Gly
        195                 200                 205

Pro Thr Arg Asp Gly Arg Ile Lys Pro Asp Val Met Ala Pro Gly Thr
    210                 215                 220

Tyr Ile Leu Ser Ala Arg Ser Ser Leu Ala Pro Asp Ser Ser Phe Trp
225                 230                 235                 240

Ala Asn His Asp Ser Lys Tyr Ala Tyr Met Gly Gly Thr Ser Met Ala
                245                 250                 255

Thr Pro Ile Val Ala Gly Asn Val Ala Gln Leu Arg Glu His Phe Val
            260                 265                 270

Lys Asn Arg Gly Val Thr Pro Lys Pro Ser Leu Leu Lys Ala Ala Leu
        275                 280                 285
```

```
Ile Ala Gly Ala Ala Asp Val Gly Leu Gly Phe Pro Asn Gly Asn Gln
    290             295             300

Gly Trp Gly Arg Val Thr Leu Asp Lys Ser Leu Asn Val Ala Phe Val
305             310             315             320

Asn Glu Thr Ser Pro Leu Ser Thr Ser Gln Lys Ala Thr Tyr Ser Phe
            325             330             335

Thr Ala Gln Ala Gly Lys Pro Leu Lys Ile Ser Leu Val Trp Ser Asp
            340             345             350

Ala Pro Gly Ser Thr Thr Ala Ser Leu Thr Leu Val Asn Asp Leu Asp
        355             360             365

Leu Val Ile Thr Ala Pro Asn Gly Thr Lys Tyr Val Gly Asn Asp Phe
    370             375             380

Thr Ala Pro Tyr Asp Asn Asn Trp Asp Gly Arg Asn Asn Val Glu Asn
385             390             395             400

Val Phe Ile Asn Ala Pro Gln Ser Gly Thr Tyr Thr Val Glu Val Gln
            405             410             415

Ala Tyr Asn Val Pro Val Ser Pro Gln Thr Phe Ser Leu Ala Ile Val
            420             425             430

His
```